United States Patent [19]
Henderson

[11] Patent Number: 5,567,227
[45] Date of Patent: Oct. 22, 1996

[54] METHOD FOR IMPROVING THE RANGE OF STABLE CONTROL OF THE PNEUMATIC SYSTEM OF A GAS CHROMATOGRAPH

[75] Inventor: Robert C. Henderson, Avondale, Pa.

[73] Assignee: Hewlett-Packard Company, Palo Alto, Calif.

[21] Appl. No.: 376,616

[22] Filed: Jan. 23, 1995

[51] Int. Cl.⁶ ........................................ B01D 15/08
[52] U.S. Cl. ........................ 95/22; 95/82; 96/102; 96/103
[58] Field of Search ............... 73/23.24, 23.27, 73/23.36; 95/19, 22, 23, 82; 96/102, 103

[56] References Cited

U.S. PATENT DOCUMENTS

| | | | |
|---|---|---|---|
| 4,230,464 | 10/1980 | Bonmati et al. | 95/22 |
| 4,802,981 | 2/1989 | Kenney et al. | 96/102 X |
| 4,820,317 | 4/1989 | Fahey | 95/22 |
| 4,994,096 | 2/1991 | Klein et al. | 96/102 X |
| 5,108,466 | 4/1992 | Klein et al. | 96/102 X |
| 5,133,859 | 7/1992 | Frank et al. | 96/102 X |
| 5,163,979 | 11/1992 | Patrick et al. | 95/19 |
| 5,391,221 | 2/1995 | Fukushima et al. | 96/102 X |
| 5,431,712 | 7/1995 | Henderson et al. | 96/102 X |

FOREIGN PATENT DOCUMENTS

1214627 12/1970 United Kingdom ............ 96/102

*Primary Examiner*—Robert Spitzer
*Attorney, Agent, or Firm*—Pamela Lau Kee

[57] ABSTRACT

A frequency response of a pneumatic system used to control a gas chromatograph may be determined by applying a loop-closed direct method. The loop-closed direct method can be used to describe a frequency response of a time-invariant, linear system and predicting the system stability for any input signal. The transfer function which describes the frequency response is used by a microprocessor to control the physical parameters of the pneumatic system in terms of pressure and flow.

8 Claims, 7 Drawing Sheets

METHOD FOR IMPROVING THE RANGE OF STABLE CONTROL OF THE PNEUMATIC SYSTEM OF A GAS CHROMATOGRAPH

FIELD OF THE INVENTION

The present invention pertains to method for controlling the pneumatic system associated with a gas chromatograph. More particularly, the invention specifically relates to a method for characterizing the physical parameters of the pneumatic system, and using that information in real time to modify the controller parameters thus increasing the range of stable operation of a closed-loop pneumatic control system.

BACKGROUND OF THE INVENTION

In analytical chemistry, liquid chromatography (LC) and gas chromatography (GC) techniques have become important tools in the identification of chemical sample components. The basic principle underlying all chromatographic techniques is the separation of a sample chemical mixture into individual components by transporting the mixture in a carrier fluid through a porous retentive media. The carrier fluid is referred to as the mobile phase and the retentive media is referred to as the stationary phase. The principal difference between liquid and gas chromatography is that the mobile phase is either a liquid or a gas, respectively.

In a GC apparatus, an inert carder gas typically is passed through a temperature-controlled column which contains a stationary phase in the form of porous sorptive media. Gas chromatography columns have also been known to comprise a hollow capillary tube having an inner diameter in the range of few hundred microns coated with the stationary phase. A sample of the subject mixture is injected through an inlet into the carrier gas stream and passed through the column. As the subject mixture passes through the column, it separates into its various components. Separation is due primarily to differences in the partial pressures of each sample component in the stationary phase versus the mobile phase. These differences are a function of the temperature within the column. A detector, positioned at the outlet end of the column, detects each of the separated components contained in the carrier fluid as they exit the column.

Inlet pressure and flow setpoints for chromatographic analysis which are controlled electronically by a pneumatic closed-loop controller offer increased precision and ease of use because there is a large dynamic range of use in terms of pressure/flow combinations. This large dynamic range of applications has a substantial effect on the natural response of the pneumatic system with respect to changes in the drive to the electronic valve used by the electronic controller to change inlet pressures or flows. The pneumatic response (pressure or flow) to a change in valve drive can be considered as a transfer function. This response is a function of frequency and is termed its "frequency response". In addition to pressure and flow, other variables within the inlet also have significant effects on the frequency response of the inlet pneumatics, which is described in terms of gain and bandwidth. These variables include tank pressure (which primarily effects gain), the gas type (which effects gain and bandwidth), the liner type and packing (which effects gain and bandwidth), the presence and type of chemical trap in the split line (effects gain and bandwidth), and the "flow gain" of the proportional valve (which primarily effects gain). This large dynamic range and many interdependent variables present a problem for the designer of the proportional integral derivative (PID) compensation loops for the inlet pressure and flow controllers. If the PID coefficients are optimized for stability with the worst case conditions, the performance is sluggish for customers who do not use the inlet under these worst case conditions. Tuning the PID loops to control the inlet for the "typical cases" may result in unstable operation for analyses operated at the fringes of "user space" or where the customer selected gas types, liner types, chemical traps, etc. result in the worst case conditions for stability. As users change the inlet configuration, the pressure control of the inlet can begin to oscillate.

For any pneumatic system, when flow is increased, the "gain" of the inlet increases, and that as the pressure of the inlet is increased, the "bandwidth" of the inlet increases. Both of these terms significantly effect the control coefficients for the electronic control loop of the inlet pneumatics. For example, if the proportional integral derivative (PID) controller gain is too large, at high inlet flows (i.e. high "gain" conditions), the inlet flows may oscillate due to too much overall gain. Correspondingly, if the PID compensation is properly "tuned" for a high pressure case, and the pressure setpoint is changed to a low pressure (i.e. "bandwidth" conditions), the pressure control loop could oscillate due to too much phase shift within the system.

Figure 1:
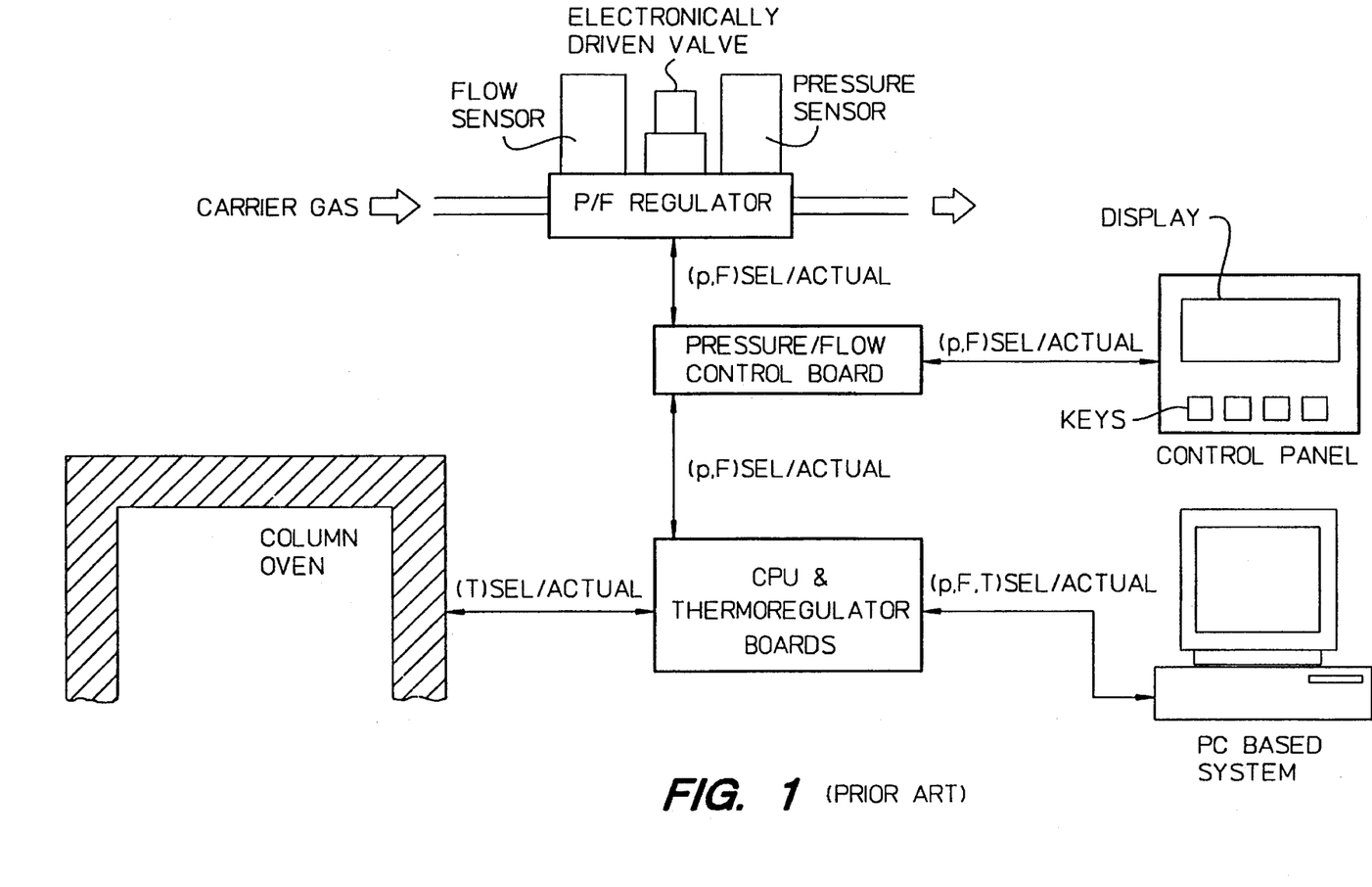
FIG. 1 illustrates a functional block diagram of a prior art solution.

FIG. 1 illustrates a functional block diagram of the pneumatic system solution offered by Fisons. The inlet has only one electronic control loop, either pressure or flow, and a mechanical pressure regulator across one of two restrictors (R1, R2) for controlling split vent flow. The system has a single electronic control loop that controls either pressure or flow and lacks programmable flexibility. It can not compensate for the effect of one variable on the other (e.g. high "gain" conditions caused by high flow setpoints can not be used to compensate a pressure control loop). Furthermore, there are a large number of components in the sample path. Not only does each component shrink the available user space, each component adds a variable to the transfer function can effect the stability of the single electronic control loop.

Figure 2:
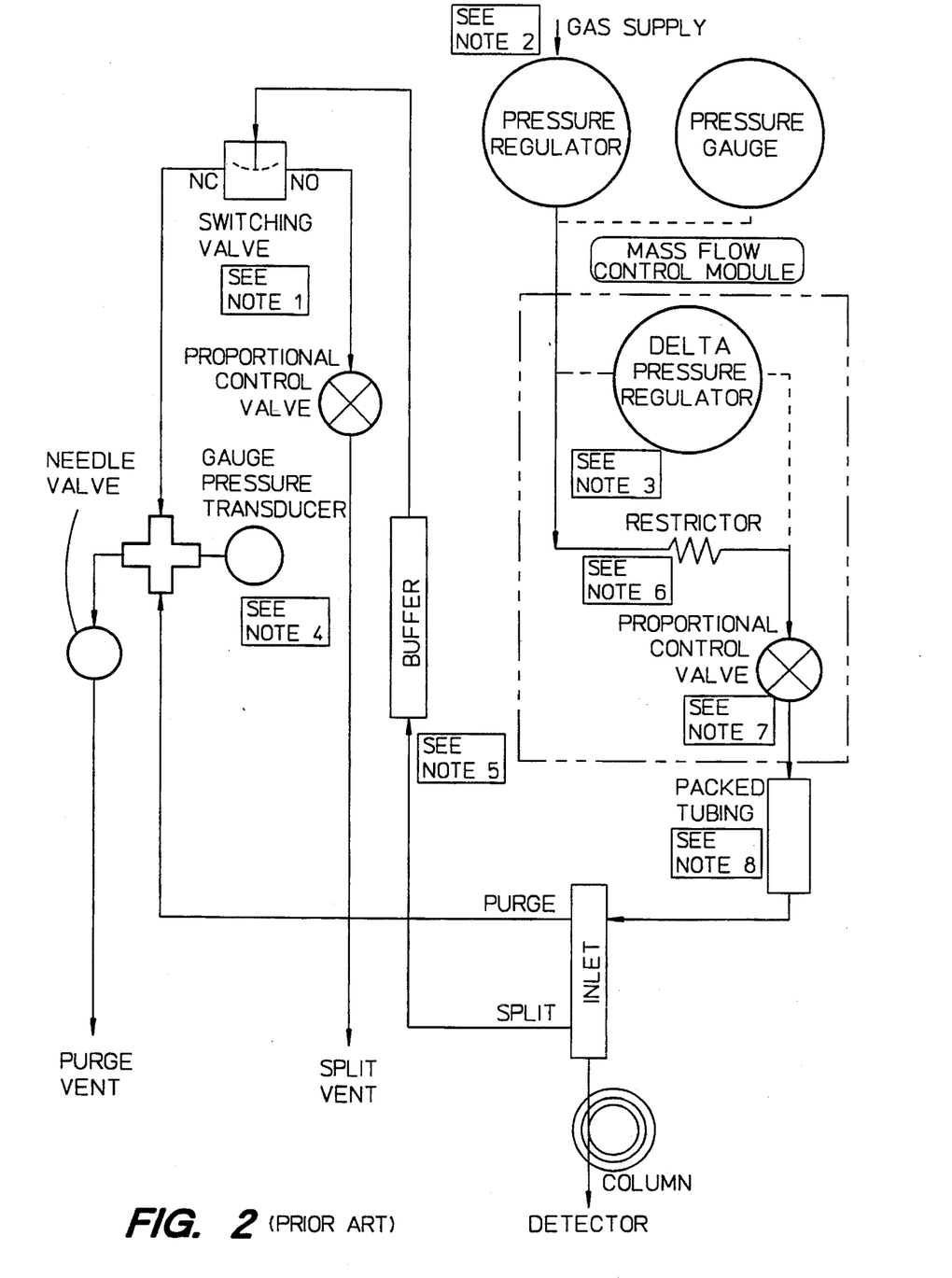
FIG. 2 illustrates a functional block diagram of another prior art solution.

Another technique for electronic control is shown in FIG. 2, a functional block diagram of the Shimadzu 17A, a split/splitless inlet gas chromatograph, manufactured by Shimadzu. A mass flow controller is connected at the input to the inlet and a back pressure regulator is connected at the output of the inlet. A buffer and packed tubing are included in this system. Although the control loops are programmable, the addition of the buffer and packing tubing reduces the bandwidth and thus increases the response time of the inlet to setpoint changes or disturbances rejection (such as the pressure "pulse" that happens during vaporization of the injected solvent).

It would be beneficial to characterize the pneumatic system of a gas chromatograph as a transfer function in which all of the variables are described in terms of either pressure or flow. It would be an additional benefit if the transfer function were used to alter the electronic control of the pneumatic system to improve the stability of the system and the response time to setpoint changes over a broad range of user pressure and flow setpoints.

SUMMARY OF THE INVENTION

A pneumatic system incorporating electronic valves and sensors can be thought of as a "black box" where the input is a voltage to the electronic valve, and the output is the output of the electronic pressure or flow sensor. The relationship of the output to the input of this "black box" is commonly referred to as its transfer function. Transfer functions of most physical systems are frequency dependent (i.e. the output to input relationship changes as a function of the input frequency). The frequency response of the pneumatic system used to control a gas chromatograph may be determined by applying a loop-closed direct method of measurement. The frequency response can be used to determine the system stability of a linear, time-invariant system when an input signal is applied. A swept frequency sine wave is applied to the input of a closed-loop controller. Both voltage going to the electronic valve (the input to the pneumatic "black box") and output of the pressure or flow sensor (the output of the pneumatic "black box") is measured. By dividing the output signal by the input signal, the frequency response, described as a transfer function, can be calculated. Both the magnitude and phase information can be generated for the frequency response.

The frequency response is determined for a range of user selectable pressure and flow settings and a series of hardware operational parameters. The magnitude and phase plots are determined for each combination. The plots when combined describe the overall frequency response of the pneumatic "black box". The overall frequency response may be used in a table of frequency cardinal points as a function of the hardware operational parameters, flow, and pressure. Because the gain and phase of the frequency response depends upon the flow and pressure setpoints, these parameters were chosen as inputs for the transfer function. A compensating table, in which each variable is described as a function of flow and pressure, is used to alter the control the system to increase the range of operation.

The PID controller selects a correcting gain multiplier from the compensating table to apply to the overall output of the controller terms. In one embodiment, the frequency response is described in terms of flow, because the gain of the system depends the most on this variable. The resulting controller error calculations are then multiplied by the correcting gain multiplier, which is used to adjust the effect of the flow setpoint on the pneumatic system. For example, if the flow is set to a low value (where the gain of the pneumatic system is very low), the PID controller will generate a large multiplier term, so that the controller output is larger for the lower gain systems (this keeps the overall gain of the control loop stable).

Both pressure and flow controllers for the pneumatic system use the above method for characterization during each PID calculation. Additionally, the pressure controller further corrects the PID coefficients to account for changes in bandwidth as the pressure setpoint is varied. Dynamically adjusting the PID coefficients as a function of the pressure and flow setpoints provides optimum PID coefficients across a broad range of user setpoints. That is, the user may more optimally control the pneumatic system according to its transfer function by specifying the desired pressure and flow values.

DETAILED DESCRIPTION OF THE PREFERRED EMBODIMENTS

Figure 3A:
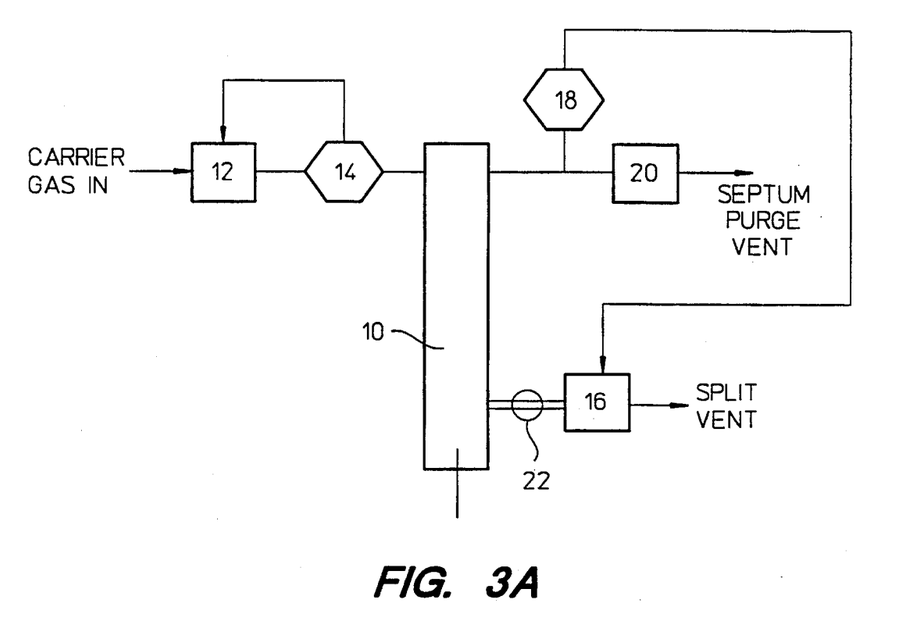
FIG. 3A and 3B illustrate functional block diagrams for a pneumatic system used to govern a gas chromatograph inlet.
Figure 3B:
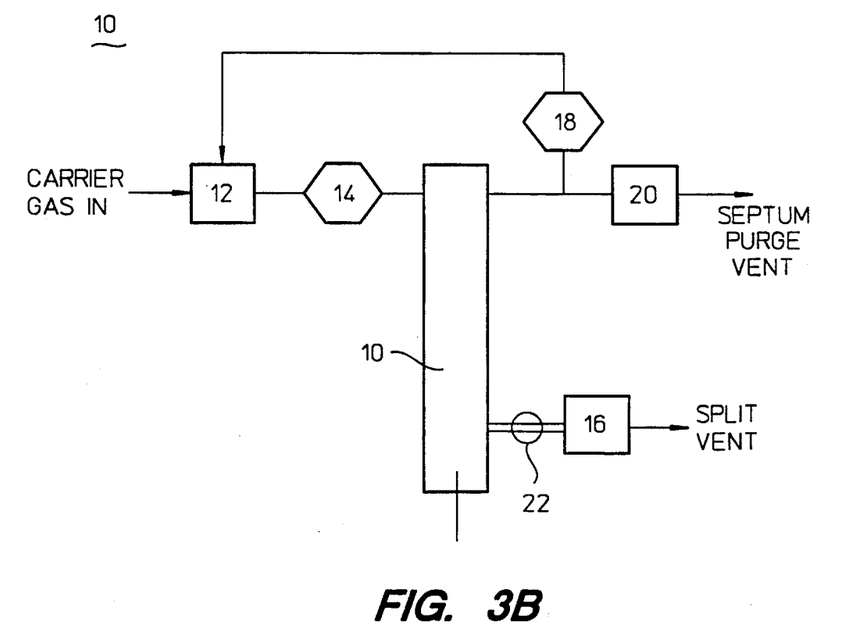

FIGS. 3A and 3B illustrate functional block diagram for a pneumatic system used to govern a gas chromatograph.

FIG. 3A illustrates split mode operation of the pneumatic system 10, a first proportional valve 12 acts as a mass flow controller for the total inlet flow as measured by a flow sensor 14. A second proportional valve 16 behaves as a back pressure regulator by controlling the inlet pressure as measured by a pressure sensor 18. A "black box" regulator 20 controls the septum purge flow. This is the split configuration that is used with the split/splitless inlet.

FIG. 3B illustrates splitless injection operation of the pneumatic system 10, the first proportional valve 12 controls the pressure as measured by the pressure sensor 18. A valve 22 is an on/off valve which is turned off so there is no flow out of the split vent. The second proportional valve 16 is turned on at a nominal value so that there is no back pressure on the valve 22. The flow sensor 14 measures total flow, but does not control the first proportional valve 12. In this configuration, the total flow into the inlet is the column flow and septum purge flow.

Figure 4:
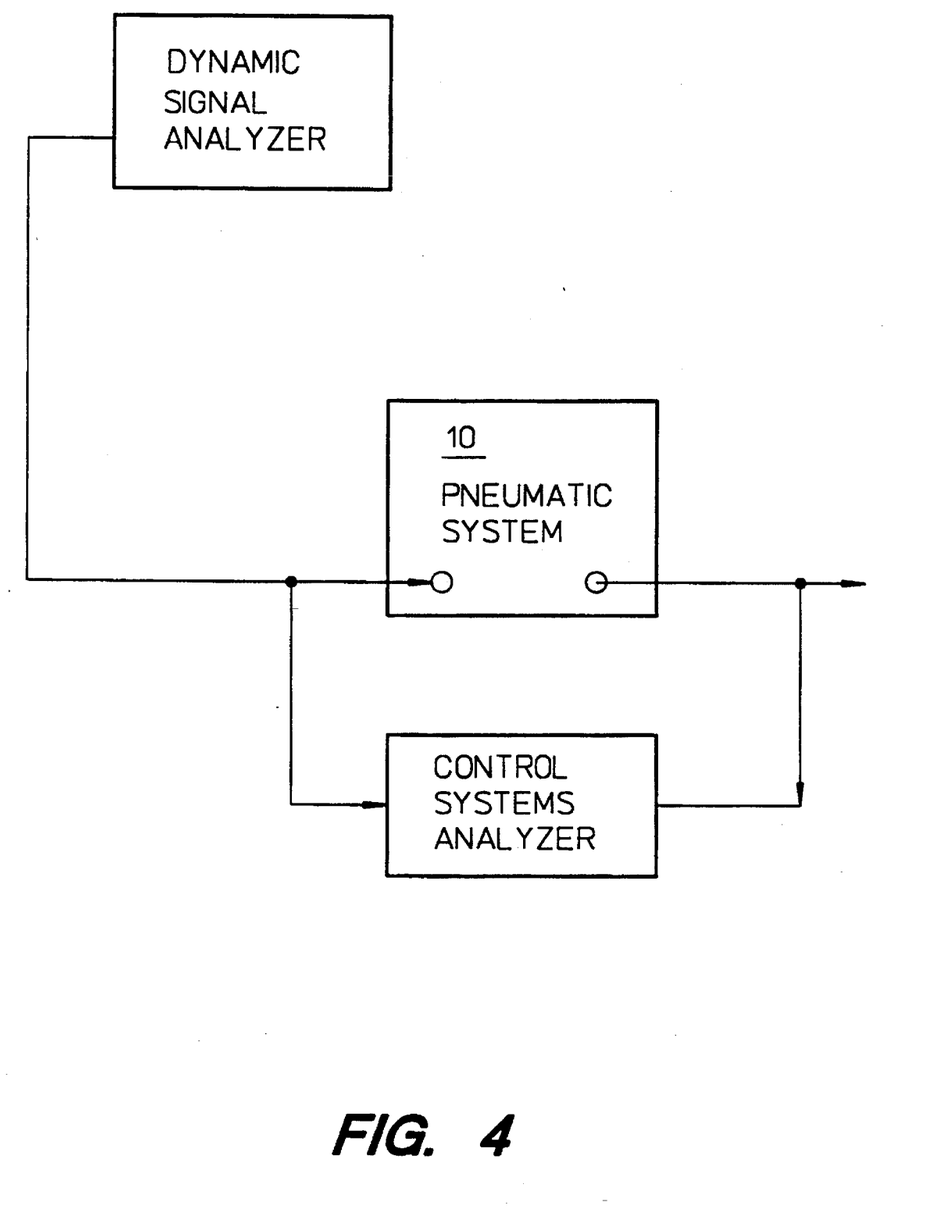
FIG. 4 illustrates the loop-closed direct method as applied to the pneumatic system shown in FIGS. 3A and 3B.

FIG. 4 is a block diagram used to characterize the frequency response of the pneumatic system 10 shown in FIGS. 3A and 3B. The pneumatic system 10 is tested at various points using the loop-closed direct method with a dynamic signal analyzer to derive an open-loop frequency response of the system. The loop-closed direct method is used to describe a frequency response of a time-invariant, linear system and to predict the system stability for any input signal.

A dynamic signal analyzer applies a swept frequency sine wave to the input of a closed-loop controller. A control systems analyzer monitors both the voltage going to the electronic valve (the input to the pneumatic system) and also monitors the output of the pressure or flow sensor (the output of the pneumatic system). By dividing the output signal by the input signal, the frequency response, described as a transfer function, for the pneumatic system can be calculated. Both the magnitude and phase information are generated for the frequency response.

The frequency response is evaluated for range of user selectable pressure and flow settings and a series of hardware operational parameters such as with and without chemical trap, 3 types of inlet liners, clean vs. dirty chemical trap, column length, column diameter, and gas type. The magnitude and phase plots are determined for each combination. The plots when combined describe the overall frequency response of the pneumatic system.

The overall frequency response may be used in a table of frequency cardinal points as a function of gas type, liner type, column length and diameter, flow, and pressure. Because the gain and amplitude of the frequency response depends on the flow and pressure settings, these parameters were chosen as selectable inputs for the non-linear characterization. A compensating table, in which each variable is described as a function of flow or pressure, is used to control the system.

The PID controller uses the compensating table to look-up a correcting gain multiplier that is applied to the overall output of the controller terms. In one embodiment, the input pointer to this table is described in terms of a flow value, because the gain of the system is most dependent on this variable. The resulting controller error calculations are then multiplied by the correcting gain multiplier, which is used to adjust the gain of the controller to make the loop-gain of the pneumatic system independent of the flow setpoint of the gas chromatograph. For example, if the flow is set to a low value (where the gain of the pneumatic system is very low), the table look-up will generate a large multiplier term, so that the controller output is larger for the lower gain systems (this keeps the overall gain of the control loop stable).

For each control loop (e.g. pressure or flow), four values are specified for the PID control loops. The first three terms are the proportional (P), integral (I), and derivative (D) coefficients and the last is a non-linear coefficient. This last term is used to either "look-up" into a gain table or goes directly into a calculation to determine a PID change.

Pressure controller PID terms are altered for both gain and bandwidth effects while flow controller PID terms are only altered for gain effects. A nonlinear gain compensation term is used to look-up into the gain table. This term decreases the gain of the P, I, and D terms for both pressure and flow PID controllers as the total inlet flow increases. A linear bandwidth compensation term is used to either increase the I term while decreasing the D term or decrease the I term while increasing the D term. Thus, the direction that the "zeros" of the transfer function are shifted of the PID controller is determined by the inlet pressure setpoint. The P term remains unaffected.

In summary, both controllers, pressure and flow, for the pneumatic system use the above method for "gain" compensation during each PID calculation. Additionally, the pressure controller further corrects the PID controller terms to account for the change in bandwidth as the pressure setpoint is changed. Alternatively, a transfer function can be used rather than a table look-up for compensation.

Figure 5:
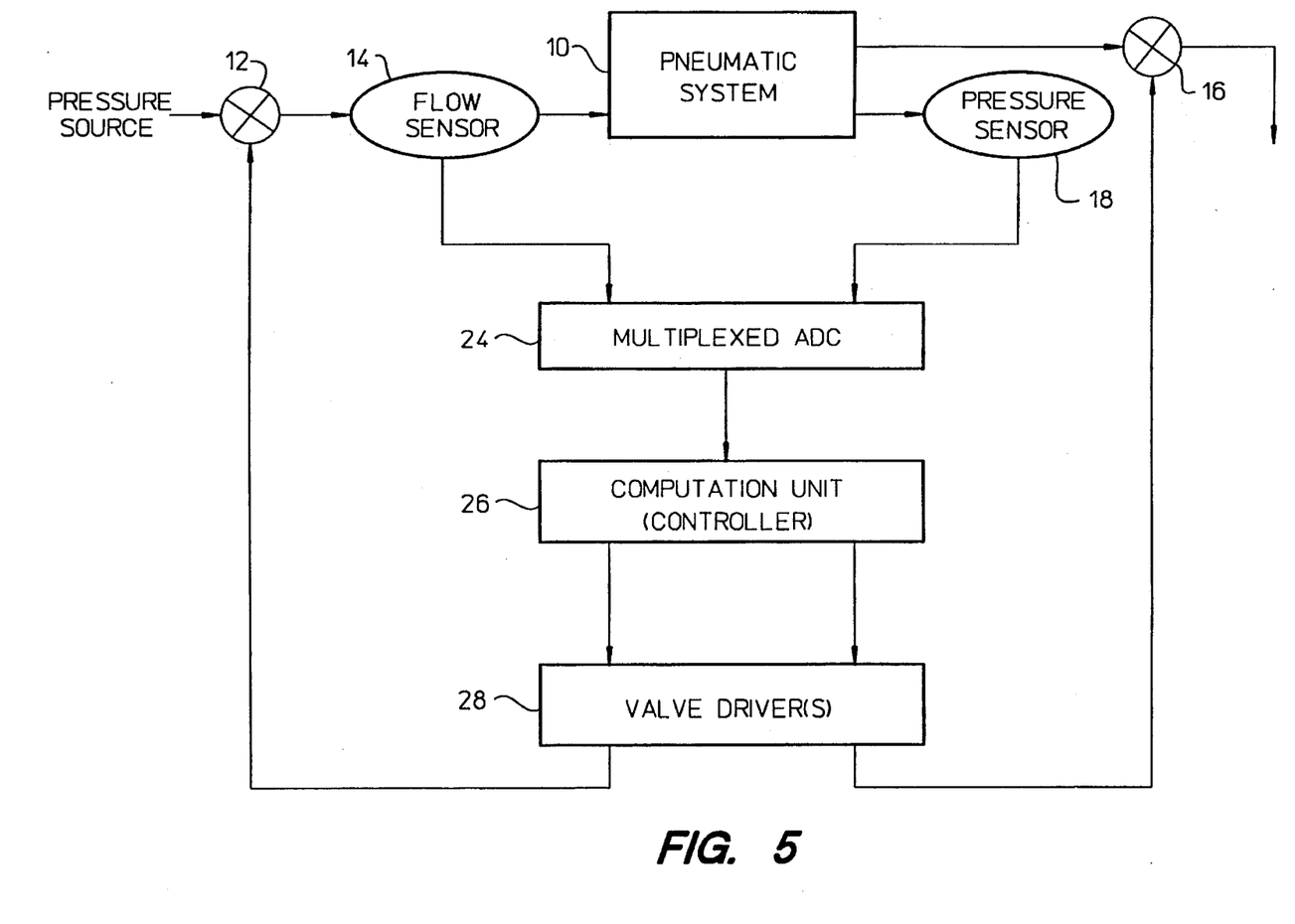
FIG. 5 shows a block diagram of a gas chromatograph split-splitless pneumatic controller which utilizes the characteristics of the pneumatics to provide a more stable pneumatic control over an extended range of user setpoints.

FIG. 5 shows a block diagram of a split-splitless pneumatic system for a gas chromatograph, the HP6890 manufactured by the Hewlett-Packard Company, which utilizes the frequency response characteristics of the pneumatic system 10 to provide a more stable pneumatic control over an extended range of user setpoints. The first proportional valve 12, acting as a pressure source, is connected to a flow sensor 14. The pneumatic system 10 connects between the flow sensor 14 and the second proportional valve 16, which behaves as the back pressure regulator. The pneumatic system 10 is further connected to the pressure sensor 18. A multiplexed analog-digital converter (ADC) 24 is connected to both the flow and pressure sensors 14, 16. A controller 26 is connected between the ADC 24 and valve drivers 28. The valve drivers 28 are connected to the first and the second proportional valves 12, 16.

The ADC 24 receives analog signals from the flow sensor 14 and the pressure sensor 18. The ADC 24 converts the analog signals into digital signals, which are received by the controller 26. The controller 26 modulates the physical parameters of the pneumatic system 10 through valve signals. The valve signals are received by the valve drivers 29 which control the first and second proportional valves 12, 16.

Figure 6:
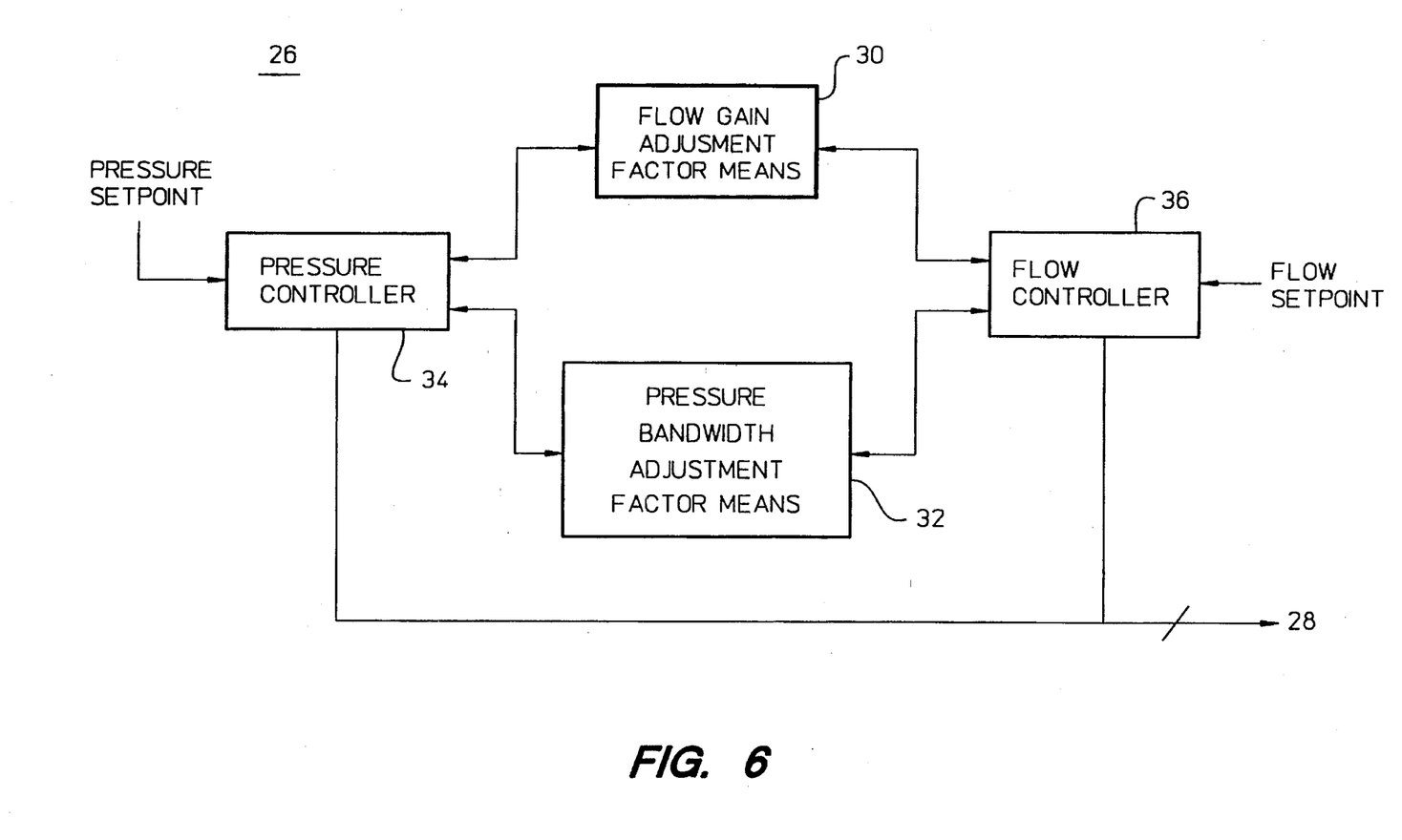
FIG. 6 shows an embodiment of a block diagram for the controller 26 shown in FIG. 5.

FIG. 6 shows an embodiment of a block diagram for the controlling means 26 shown in FIG. 5. A pressure controller 34 is connected to a flow gain adjustment factor means 30 and a pressure bandwidth adjustment factor means 32. A flow controller 36 is connected to the flow gain adjustment factor means 30 and the pressure bandwidth adjustment factor means 32.

The pressure controller 34, which generates a first valve drive signal for controlling the first proportional valve, has an associated flow gain adjustment factor and a pressure bandwidth adjustment factor. The flow controller 36, which generates a second valve drive signal for controlling the second proportional valve, has a flow gain adjustment factor and a pressure bandwidth adjustment factor. The pressure controller 34 adjusts the pressure controller compensation terms according to the flow gain adjustment factor and the pressure bandwidth adjustment factor. The flow controller 36 adjusts the flow controller compensation terms according to the flow gain adjustment factor and the pressure bandwidth adjustment factor.

The flow gain adjustment factor means 30 may be a gain look-up table, where gain is described at different pressure setpoints, or a function, in which gain is described in terms of flow. The pressure bandwidth adjustment factor means 32 may be a bandwidth look-up table, where bandwidth is described at different flow setpoints, or a function in which bandwidth is described in terms of pressure.

Figure 7:
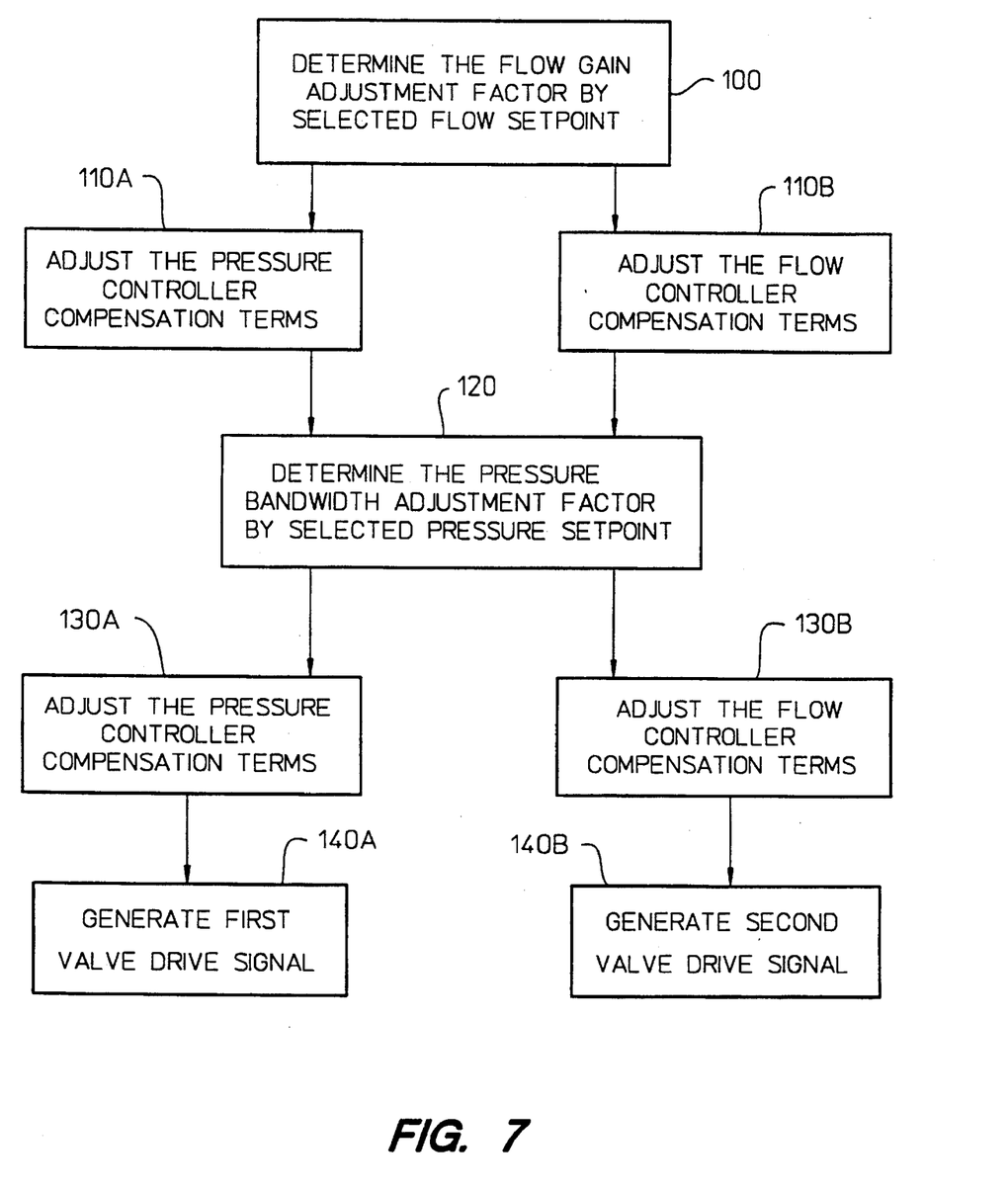
FIG. 7 illustrates a process flowchart implemented by the controller shown in FIG. 5.

FIG. 7 illustrates a process flowchart implemented by the controller shown in FIG. 5. In step 100, both the pressure controller 34 and the flow controller 36 receive the flow gain adjustment factor according to the selected flow setpoint. In step 110A, the pressure controller 34 adjusts the pressure controller compensation terms according to the flow gain adjustment factor. In step 110B, the flow controller 36 adjusts the flow controller compensation terms according to the flow gain adjustment factor. In step 120, both the pressure controller 34 and the flow controller 36 receive pressure bandwidth adjustment factor according to the selected pressure setpoint. In step 130A, the pressure controller further adjusts the pressure controller compensation terms according to the pressure bandwidth adjustment factor. In step 130B, the flow controller further adjusts the flow controller compensation terms according to the pressure bandwidth adjustment factor. In step 140A, the pressure controller generates the first valve drive signal from the final pressure controller compensation terms, the actual pressure, and the desired pressure. In step 140B, the flow controller generates the second valve drive signal from the flow controller compensation terms, the actual flow, and the desired flow.

I claim:

1. A method for dynamically varying a controller to vary the frequency response characterizing a closed-loop pneumatic system associated with a chromatograph comprising the steps of:

characterizing the optimum controller coefficients of the closed-loop pneumatic system with respect to pressure and flow setpoints to determine the frequency response of the closed-loop pneumatic system as a controller algorithm; and dynamically varying the controller according to the controller algorithm wherein the controller coefficients are altered as a function of the pressure and flow setpoints to provide a controller having optimized controller coefficients for selected pressure and flow setpoints.

2. A method for dynamically varying a controller to vary the frequency response characterizing a closed-loop pneumatic system associated with a chromatograph, as defined in claim 1, the step of characterizing the optimum controller coefficients of the pneumatic system comprising the steps of:

applying a test signal to the pneumatic system;

monitoring an output signal;

determining a transfer function that corresponds to the frequency response of the closed-loop pneumatic system by dividing the output signal by the test signal; and describing the transfer function in terms of pressure and flow.

3. A method for dynamically varying a controller to vary the frequency response characterizing a closed-loop pneumatic system associated with a chromatograph, as defined in claim 2, wherein the step of determining a transfer function further comprises the steps of:

characterizing the pneumatic system with respect to hardware parameters of the closed-loop pneumatic system; and characterizing the chromatograph with respect to user-defined parameters.

4. A method for dynamically varying a controller to vary the frequency response characterizing a closed-loop pneumatic system associated with a chromatograph, as defined in claim 2, wherein the step of describing the transfer function further comprises the step of generating a look-up table dependent upon a series of pressure and flow setpoint pairs while substantially optimizing the closed-loop performance at each pair of the series of pressure and flow setpoint pairs.

5. A method for dynamically varying a controller to vary the frequency response characterizing a closed-loop pneumatic system associated with a chromatograph, as defined in claim 2, wherein the step of describing the transfer function further comprises the step of generating a function that substantially optimizes the closed-loop performance at the selected pressure setpoint and the selected flow setpoint.

6. A method for dynamically varying a controller to vary the frequency response characterizing a closed-loop pneumatic system associated with a chromatograph, as defined in claim 1, wherein the step of dynamically varying the controller further comprises the steps of:

generating a gain compensation term with respect to the selected flow setpoint;

adjusting a pressure controller and a flow controller according to the gain compensation term;

generating a bandwidth compensation term with respect to the selected pressure setpoint;

adjusting the pressure controller and the flow controller according to the bandwidth compensation term; and generating a first and a second valve drive signal to substantially maintain a closed-loop bandwidth over a broad range of pressure and flow setpoints.

7. A closed-loop pneumatic system having a dynamically variable frequency response, comprising:

a first proportional valve;

a flow sensor connecting to the first proportional valve;

a pneumatic system, having physical properties describe as optimum controller coefficients, connecting to the flow sensor;

wherein the frequency response is described as a transfer function characterizing the optimum controller coefficients in terms of pressure and flow;

a pressure sensor connecting to the pneumatic system;

a second proportional valve connecting to the pneumatic system;

an analog-to-digital converter connecting to the flow sensor and the pressure sensor;

a controlling means for automatically varying the frequency response of the closed-loop pneumatic system according to the transfer function, connecting to the analog-to-digital converter, generating a first and a second valve drive signal;

wherein the relationship between the optimum controller coefficients and the pressure and flow setpoints is determined as a controller algorithm operative to alter the controller coefficients as a function of the pressure and flow setpoints such that the controller coefficients optimized for the current pressure and flow setpoints; and valve driving means for controlling the first and the second proportional valves, connecting between the first and the second proportional valves and the controlling means, receiving the first and the second valve drive signals and adjusting the first and the second proportional valves accordingly.

8. A closed-loop pneumatic system having a dynamically variable frequency response, the controlling means, as defined in claim 7, further comprising:

a pressure controller, having a pressure controller compensation terms, generating the first valve drive signal;

a flow controller, having a flow controller compensation terms, generating the second valve drive signal;

a gain compensation means, connecting to the pressure controller and the flow controller, for adjusting the pressure controller compensation terms and the flow controller compensation terms according to the selected flow setpoint; and a bandwidth compensation means, connecting to the pressure controller and the flow controller, for adjusting the pressure controller compensation terms and the flow controller compensation terms according to the selected pressure setpoint.

* * * * *